United States Patent [19]

Nielsen et al.

[11] Patent Number: 4,981,694
[45] Date of Patent: Jan. 1, 1991

[54] PENICILLIN PREPARATION FOR RECTAL ADMINISTRATION

[75] Inventors: Nils V. Nielsen, Avlum; Carsten Thordal, Ry; John E. Faber, Svendborg; Arne M. Pedersen, Vanlose, all of Denmark

[73] Assignee: Pharma-Vinci A/S, Frederiksverk, Denmark

[21] Appl. No.: 376,820

[22] Filed: Jul. 7, 1989

[30] Foreign Application Priority Data

Jul. 7, 1988 [DK] Denmark .............................. 3791/88

[51] Int. Cl.$^5$ ................................................. A61F 9/02
[52] U.S. Cl. ...................................... 424/436; 424/434
[58] Field of Search ............... 424/456, 458, 422, 436, 424/489, DIG. 15; 514/43, 157

[56] References Cited

U.S. PATENT DOCUMENTS

| | | | |
|---|---|---|---|
| Re. 31,926 | 6/1985 | Wetzel et al. | 514/157 |
| 4,022,889 | 5/1977 | Bannister et al. | 514/43 |
| 4,250,169 | 2/1981 | Hosoi et al. | 424/DIG. 15 |
| 4,338,306 | 7/1982 | Kitao et al. | 424/DIG. 15 |
| 4,402,692 | 9/1983 | Takagishi et al. | 424/436 |

FOREIGN PATENT DOCUMENTS

| | | |
|---|---|---|
| 138975 | 11/1978 | Denmark . |
| 2619756 | 5/1975 | Fed. Rep. of Germany . |
| 1376283 | 12/1974 | United Kingdom . |
| 1462399 | 1/1977 | United Kingdom . |

OTHER PUBLICATIONS

Article "Rectal Absorption of Benzylpenicillin", K. Backe-Hansen, pp. 170–173.

*Primary Examiner*—Merrell C. Cashion, Jr.
*Assistant Examiner*—D. Gabrielle Phelan
*Attorney, Agent, or Firm*—Ladas & Parry

[57] ABSTRACT

Penicillin preparation for rectal administration containing benzylpenicillin and sodium lauryl sulphate in a hard gelatin capsule.

6 Claims, No Drawings

PENICILLIN PREPARATION FOR RECTAL ADMINISTRATION

FIELD OF THE INVENTION

The present invention concerns a penicillin preparation for rectal administration containing penicillin and sodium lauryl sulphate.

BACKGROUND ART

Penicillin is normally given either as injection or in the form of mixture. However both are unsuited for children, either because they are afraid of being pricked or because they dislike the taste which may result in vomiting.

Also adults may have difficulty ingesting penicillin orally, and treatment with injections can only be carried out by specially trained personnel. Consequently, there is a need for a form of penicillin which can be administered rectally.

Over the years many attempts have been made to prepare an efficient suppository with penicillin. Thus, from Danish Patent No. 138,975 is known a rectally administrable penicillin preparation which contains sulbenicillin dialkalimetal salt or carbenicillin dialkalimetal salt in an oil or fat basis containing a non-ionic surface active agent.

From German published application No. 2,619,756 is known a rectally administrable penicillin preparation which contains 6-[D-(-)-α-(4-oxo-4H-thiopyran-3-ylcarboxamido)-p-hydroxyphenyl acetamido]-penicillanic acid in an oily suppository basis.

From British Patent No. 1,462,399 is known a rectally administrable penicillin preparation which contains cephalexin in an oil soluble or water soluble suppository basis which may be placed in a soft gelatin capsule.

Finally, K. Backe-Hansen in Scandinav. J. Clin. & Lab. Investigation, 170-173, 9, 1957, has described experiments with rectal absorption of benzylpenicillin in which was used a suppository basis of triglycerides containing benzylpenicillin sodium together with sodium lauryl sulphate, the latter supposedly having the effect of lowering the surface tension so that a better contact between the penicillin and the mucosa of the rectum is obtained and of inhibiting the decomposition of penicillin by penicillinase in rectum. The investigation has never resulted in a commercial product. The reason for this may be that the stability of pencillin in cast suppositories is not always good, that cast suppositories must be able to melt at body temperature which renders them rather temperature sensitive, and that production costs are high.

SUMMARY OF THE INVENTION

According to the invention a rectally administrable penicillin preparation has now been provided which does not have the above mentioned drawbacks, and which in preliminary experiments with animals and in clinical experiments has turned out to give a serum penicillin concentration of the same order as that obtained by intramuscular injection.

The penicillin preparation according to the invention is characterized in that it contains powdery benzylpenicillin or its alkali metal salts in admixture with sodium lauryl sulphate in a hard gelatin capsule.

According to the invention the penicillin is preferably benzylpencillin sodium since this has turned out to be absorbed best.

EXAMPLE

Four minipigs having a weight of 13-16 kilos, two males and two females, had inserted a hard gelatin capsule containing a mixture of 140,000 I.E. of benzylpenicillin sodium (84 mg) and 75 mg of sodium lauryl sulphate, and the serum concentration was than measured after 0.25; 0.5; 1 and 2 hours. 14 days later the same four minipigs were injected intramuscularly with 2.5 ml of benzylpenicillin containing 56,000 I.E./ml, i.e. likewise 140,000 I.E. benzylpenicillin sodium, and the serum concentration was measured after 0.25; 0.5; 1 and 2 hours. The results are shown in the following tables:

TABLE 1

Serum concentration of penicillin after rectal application of hard gelatin capsule with benzylpenicillin sodium + sodium lauryl sulphate.

| Pig No. | Penicillin serum concentration (μg/ml) hours after dosing | | | | |
|---|---|---|---|---|---|
| | 0 | 0.25 | 0.5 | 1 | 2 |
| 1. ♀ | 0 | 0 | 0.19 | 0 | — |
| 2. ♀ | 0 | 0 | 0.85 | 0.69 | 0 |
| 3. ♂ | 0 | 0.85 | 1.82 | 0.70 | 0.30 |
| 4. ♂ | 0 | 0 | 2.41 | 2.26 | 0.60 |
| mean | 0 | 0.21 | 1.32 | 0.91 | 0.23 |

TABLE 2

Serum concentration of pencillin after intramuscular application of benzylpenicillin sodium

| Pig No. | Penicillin serum concentration (μg/ml) hours after dosing | | | | |
|---|---|---|---|---|---|
| | 0 | 0.25 | 0.5 | 1 | 2 |
| 1. ♀ | 0 | 7.99 | 2.93 | 0.41 | 0 |
| 2. ♀ | 0 | 10.88 | 3.66 | 0.83 | 0 |
| 3. ♂ | 0 | 10.12 | 5.61 | 2.45 | 0.74 |
| 4. ♂ | 0 | 12.61 | 5.05 | 1.30 | 0.26 |
| mean | 0 | 10.40 | 4.31 | 1.25 | 0.25 |

It can be seen from these tables that 1 and 2 hours after application there is obtained largely the same serum concentration in the two ways of treatment. By the use of a hard gelatin capsule, however, only about ⅓ of the amount of penicillin is absorbed which is absorbed by intramuscular injection.

This can be compensated for by the use of more penicillin units per capsule. A preferred embodiment of the preparation according to the invention is characterized in that it contains 500,000 international units of benzylpenicillin sodium + 100 mg of sodium lauryl sulphate in a hard gelatin capsule.

The penicillin preparation according to the invention was further investigated by the following clinical experiments.

Capsules containing 500,000 international units of benzylpenicillin and 100 mg of sodium lauryl sulphate were used.

The subjects of the experiments were healthy adult volunteers at the age of 20-65 years who were assigned the code numbers A, B, C, D, E, F, G, H, I, M, N, O.

The individuals were given either 1 or 2 capsules and were instructed to moisten the capsules and insert them into the rectum. The capsules should be pushed so far up that they could not be felt in the rectum by tightening the sphincter afterwards.

After introduction of the capsules the individuals were asked to note the time and to observe and register possible side effects.

Subsequently blood samples were taken alternately from the right and the left cubital vein after 15 min., 30 min., 45 min., 60 min., 90 min., 120 min., 180 min. and 240 min.

The samples were marked with the individuals's code numbers and the time and were then centrifuged and kept frozen. The pencillin concentrations were determined at Statens Seruminstitut to which the samples were sent in the frozen condition.

The results are shown in tables 3 and 4 below.

None of the individuals observed any side effects.

TABLE 3

Plasma concentrations in μg/ml after rectal administration of 1,000,000 I.E. of benzylpenicillin + 200 mg of sodium lauryl sulphate.

|   | 0 | 15 | 30 | 45 | 60 | 90 | 120 | 180 | 240 min. |
|---|---|---|---|---|---|---|---|---|---|
| A | 0 | 0 | 0.047 | 0.3 | 1.2 | 2.2 | 1.8 | 0.76 | 0.28 |
| B | 0 | 0 | 1.1 | 1.5 | 1.5 | 0.38 | 0.29 | 0.14 | 0.070 |
| C | 0 | 0 | 2.1 | 4.4 | 2.9 | 0.56 | 0.30 | 0.11 | 0.038 |
| D | 0 | 0.058 | 1.6 | 2.6 | 2.3 | 0.92 | 0.39 | 0.12 | 0.029 |
| E | 0 | 0.31 | 2.1 | 2.8 | 1.9 | 0.50 | 0.45 | 0.44 | 0.92 |
| F | 0 | 0.02 | 1.75 | 4.1 | 1.9 | 0.3 | 0.21 | 0.066 | 0.032 |
| G | 0 | 0 | 0.27 | 0.72 | 0.78 | 0.68 | 0.45 | 0.1 | 0.029 |
| H | 0 | 0 | 0.56 | 1.6 | 1.5 | 0.78 | 0.22 | 0.084 | 0.029 |
| I | 0 | 0.07 | 1.7 | 4.0 | 1.8 | 0.82 | 0.23 | 0.072 | 0 |
| $\bar{X}$ | 0 | 0.05 | 1.25 | 2.44 | 1.75 | 0.80 | 0.48 | 0.21 | 0.16 |
| s | 0 | 0.10 | 0.78 | 1.31 | 0.62 | 0.56 | 0.50 | 0.24 | 0.30 |

$\bar{X}$ = mean
s = scatter

TABLE 4

Plasma concentration in μg/ml after rectal administration of 500,000 I.E. benzylpenicillin + 100 mg of sodium lauryl sulphate.

|   | 0 | 15 | 30 | 45 | 60 | 90 | 120 | 180 | 240 min. |
|---|---|---|---|---|---|---|---|---|---|
| D | 0 | 0.14 | 0.72 | 0.92 | 0.62 | 0.42 | 0.26 | 0.048 | 0.018 |
| K | 0 | 0 | 0.52 | 0.76 | 0.90 | 0.50 | 0.29 | 0.11 | 0.064 |
| M | 0 | 0 | 2.2 | 2.5 | 2.1 | 0.61 | 0.32 | 0.15 | 0.052 |
| N | 0 | 0.12 | 0.52 | 0.72 | 0.54 | 0.44 | 0.37 | 0.11 | 0.024 |
| O | 0 | 0.062 | 1.0 | 2.2 | 1.5 | 0.65 | 0.39 | 0.27 | 0.14 |
| $\bar{X}$ | 0 | 0.06 | 0.99 | 1.42 | 1.13 | 0.52 | 0.33 | 0.14 | 0.06 |
| s | 0 | 0.07 | 0.70 | 0.86 | 0.66 | 0.10 | 0.05 | 0.08 | 0.05 |

$\bar{X}$ = mean
s = scatter

We claim:
1. A preparation for rectal administration comprising powdery benzylpenicillin or at least one alkali metal salt of benzylpenicillin in admixture with sodium lauryl sulphate in a hard gelatin capsule.
2. A preparation as claimed in claim 1, wherein the preparation comprises benzylpenicillin sodium.
3. A preparation as claimed in claim 2, wherein the preparation contains 500,000 international units of benzylpenicillin+100 mg of sodium lauryl sulphate.
4. A method for the administration of benzylpenicillin comprising incorporating a mixture of powdered benzylpenicillin, or at least one alkali metal salt of benzylpenicillin, and sodium lauryl sulphate into a hard gelatin capsule and inserting the capsule into the rectum of a patient to be treated.
5. A method as claimed in claim 4, wherein the benzylpenicillin or alkali metal salt of benzylpenicillin is present in the mixture in an amount of about 500,000 international units, and wherein the sodium lauryl sulphate is present in an amount of about 100 mg.
6. A method as claimed in claim 4 wherein the benzylpenicillin or alkali metal salt of benzylpenicillin is benzylpenicillin sodium.

* * * * *